United States Patent [19]

Pastor et al.

[11] Patent Number: 4,636,573
[45] Date of Patent: Jan. 13, 1987

[54] HINDERED SILICON ESTER STABILIZERS

[76] Inventors: Stephen D. Pastor, Yonkers; John D. Spivack, Spring Valley, both of N.Y.

[21] Appl. No.: 773,962

[22] Filed: Sep. 9, 1985

[51] Int. Cl.$^4$ .............................. C07F 7/08; C07F 7/18
[52] U.S. Cl. .................................... 556/441; 556/427; 585/601; 252/48.4; 252/49.6; 524/261; 524/262; 524/265
[58] Field of Search ............... 556/441, 427; 252/49.6, 252/48.4; 524/265, 262, 261

[56] References Cited

U.S. PATENT DOCUMENTS 3,328,350  6/1967  Omietanski et al. ............ 556/441 X
4,176,124  11/1979  Darms et al. .................... 556/441 X Primary Examiner—Paul F. Shaver
Attorney, Agent, or Firm—Harry Falber

[57] ABSTRACT

Compounds of the formulae I and II

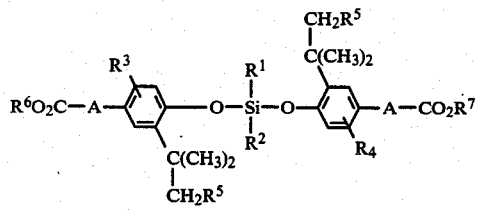

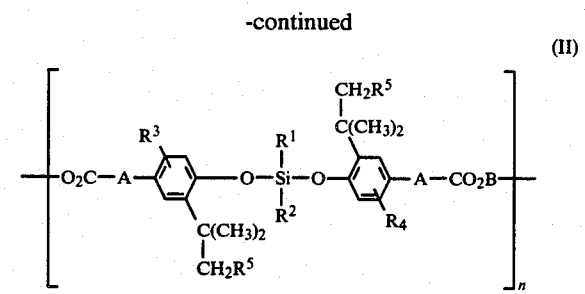

wherein
$R^1$, $R^2$, $R^3$, $R^4$ and $R^5$ are independently hydrogen, alkyl of 1 to 18 carbon atoms, cycloalkyl of 5 to 8 carbon atoms, phenyl, phenyl substituted by alkyl of 1 to 18 carbon atoms, aralkyl of 7 to 9 carbon atoms or said aralkyl substituted by alkyl of 1 to 12 carbon atoms,
$R^6$ and $R^7$ are independently alkyl having 1 to 30 carbon atoms, cycloalkyl of 5 to 8 carbon atoms, phenyl, phenyl substituted by alkyl of 1 to 18 carbon atoms, aralkyl of 7 to 9 carbon atoms or said aralkyl substituted by alkyl of 1 to 12 carbon atoms;
A is a direct bond, a methylene or an ethylene radical,
B is an alkanediyl radical of 2 to 10 carbon atoms, the radical of formula —CH$_2$CH$_2$—S—CH$_2$CH$_2$— or of the formula III

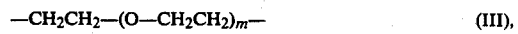

wherein m is an integer from 1 to 4, B also denotes a phenylene radical or a biphenylene radical interrupted by an oxygen or a sulfur atom or by the group of formula —C(CH$_3$)$_2$—; and
n is an integer from 2 to 100.

13 Claims, No Drawings

HINDERED SILICON ESTER STABILIZERS

The present invention relates to new hindered silicon esters, to their manufacture and use as stabilizers for organic polymers.

Silyl ester derivatives of sterically hindered phenols, as described in Chemical Abstracts 83,60454g (1975), have already been proposed as stabilizers for polyethylene. It has now been found that certain silyloxy derivatives containing at least two carboxylic ester groups are particularly efficient stabilizers against thermo-oxidative and/or light-induced degradation of polymers.

Accordingly, the object of the present invention relates to compounds of the formulae I and II

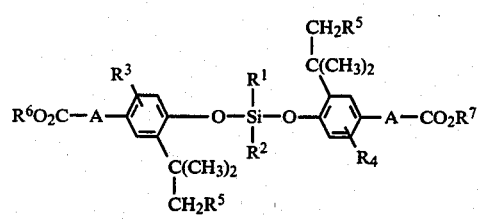
(I)

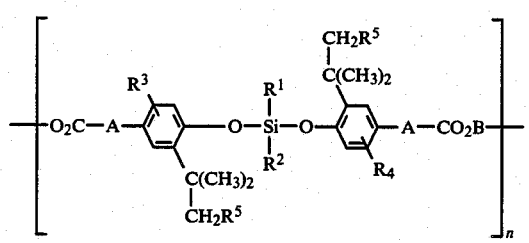
(II)

wherein $R^1$, $R^2$, $R^3$, $R^4$ and $R^5$ are independently hydrogen, alkyl of 1 to 18 carbon atoms, cycloalkyl of 5 to 8 carbon atoms, phenyl, phenyl substituted by alkyl of 1 to 18 carbon atoms, aralkyl of 7 to 9 carbon atoms or said aralkyl substituted by alkyl of 1 to 12 carbon atoms;

$R^6$ and $R^7$ are independently alkyl having 1 to 30 carbon atoms, cycloalkyl of 5 to 8 carbon atoms, phenyl, phenyl substituted by alkyl of 1 to 18 carbon atoms, aralkyl of 7 to 9 carbon atoms or said aralkyl substituted by alkyl of 1 to 12 carbon atoms;

A is a direct bond, a methylene or an ethylene radical,

B is an alkanediyl radical of 2 to 10 carbon atoms, the radical of formula —CH$_2$CH$_2$—S—CH$_2$CH$_2$— or of the formula III $$-CH_2CH_2-(O-CH_2CH_2)_m- \quad \text{(III)},$$

wherein m is an integer from 1 to 4, B also denotes a phenylene radical or a biphenylene radical interrupted by an oxygen or a sulfur atom or by the group of formula —C(CH$_3$)$_2$—; and n is an integer from 2 to 100.

In the definition of the compounds of the formulae I and II, $R^1$, $R^2$, $R^3$, $R^4$ and $R^5$ can be alkyl of 1 to 18 carbon atoms and $R^6$ and $R^7$ can be alkyl of 1 to 18 carbon atoms such as, for example, methyl, ethyl, n-propyl, iso-propyl, butyl, sec.-butyl, tert.-butyl, 1,1-dimethylbutyl, n-heptyl, n-octyl, 2-ethylhexyl, 1,1,3,3-tetramethylbutyl, n-nonyl, n-decyl, n-undecyl, n-dodecyl, 1,1,3,3,5,5-hexamethylhexyl, n-tetradecyl, n-heptadecyl and n-hexadecyl. Particularly preferred as $R^1$ and $R^2$ is methyl and preferred $R^3$ and $R^4$ is tert.-butyl.

$R^1$, $R^2$, $R^3$, $R^4$, $R^5$, $R^6$ and $R^7$, can also be a cycloalkyl group with 5 to 8 carbon atoms such as, for example, cyclopentyl, cyclohexyl, methylcyclohexyl and cyclooctyl.

If $R^1$, $R^2$, $R^3$, $R^4$, $R^5$, $R^6$ and $R^7$ denote aralkyl of 7 to 9 carbons or said aralkyl substituted by alkyl of 1 to 12 carbon atoms, it can be, for example, benzyl, phenylethyl, dimethylbenzyl, or benzyl substituted on the phenyl group by one, two or three methyl groups.

$R^1$, $R^2$, $R^3$, $R^4$, $R^5$, $R^6$ and $R^7$ can also be a phenyl substituted by alkyl of 1 to 18 carbon atoms such as, for example, the alkyl groups already mentioned above for the definition of alkyl of 1 to 18 carbon atoms.

$R^6$ and $R^7$ can be alkyl having 1 to 30 carbon atoms such as, for example, the alkyl groups already mentioned above for the corresponding definition of the groups $R^1$ to $R^5$, and, in addition to that, n-eicosyl, n-dodecyl, n-tetracosyl or n-triacontyl. Particularly preferred $R^6$ and $R^7$ is n-dodecyl or octadecyl.

In the definition of the compounds of formula II, B can be an alkanediyl radical of 2 to 10 carbon atoms such as, for example, ethylene, propylene-1,2, propylene-1,3, tetramethylene-1,4, 1-ethylethylene, hexamethylene-1,6, octamethylene-1,8 and decamethylene-1,10. Examples of bivalent radicals of the formula III are 3-oxapentamethylene, 3,5-dioxaoctamethylene or 3,5,7-trioxa-undecamethylene.

B can also be a biphenylene radical interrupted by an oxygen or a sulfur atom or by the group —C(CH$_3$)$_2$— such as, for example 4,4'-diphenylether, 4,4'-diphenylsulfide and 4,4'-diphenyl-(dimethyl)methane.

Preferred compounds of the formulae I and II are those in which $R^1$ and $R^2$ are hydrogen or alkyl of 1 to 4 carbon atoms, $R^3$ and $R^4$ are hydrogen or alkyl of 1 to 6 carbon atoms, $R^5$ is hydrogen $R^6$ and $R^7$ are alkyl of 1 to 18 carbon atoms, A is a direct bond or an ethylene radical, B is a hexamethylene radical and n is a number from 2 to 10.

Particularly preferred compounds of the formulae I and II are those in which $R^1$ and $R^2$ are hydrogen or methyl, $R^3$ and $R^4$ are tert.-butyl in the ortho position to the phenolic oxygen atom, $R^5$ is hydrogen, $R^6$ and $R^7$ are alkyl of 10 to 18 carbon atoms, A is a direct bond, B is a hexamethylene radical and n is a number from 2 to 5.

The preparation of the compounds of formula I can be effected, for example, by reaction of one mole of a compound of the formula (IV)

(IV)

wherein Y is a chlorine or bromine atom, with one mole of a compound of the formula (V)

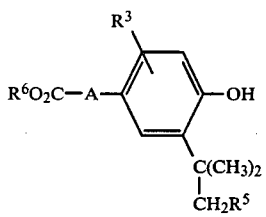

and one mole of a compound of the formula (VI)

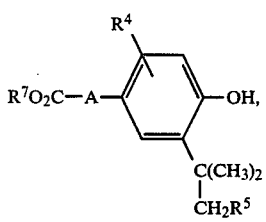

wherein $R^1$ to $R^7$ have the above-mentioned definitions.

The preparation of the compounds of formula II can be effected, for example, by reaction of one mole of the compound of the formula (VII)

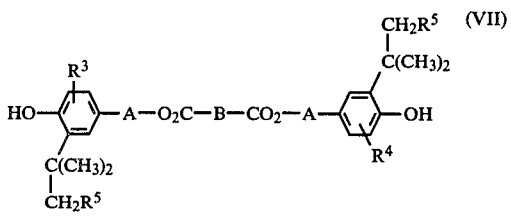

with a compound of the formula IV, wherein $R^1$ to $R^5$, A and B have the above-definitions.

The processes as described above are preferably carried out in the presence of solvents and/or diluents which are inert to the reactants. Aprotic solvents are particularly suitable such as, for example, aliphatic and aromatic hydrocarbons like hexane, cyclohexane, benzene, toluene, xylene, halogenated hydrocarbons such as chlorinated ethylene, carbon tetrachloride, chloroform, chlorobenzene, also ethers and ethereal compounds such as diethyl ether, mono-, di-, tri- and tetraethylene glycol dimethylether, mono-, di-, tri- and tetraethylene glycol diethylether or tetrahydrofuran, as well as nitriles such as acetonitrile.

Furthermore, an acid-binding agent or a cation complexing agent may be added to the reaction mixture. Suitable for this purpose are, in particular, tertiary amines such as trialkylamines, e.g. triethylamine, pyridine and pyridine bases or dialkylanilines. Suitable complexing agents are for example crown ethers.

The reaction can be carried out at various temperatures, preferably at a temperature from 0° C. to 150° C. and the reaction duration can be between a few minutes and several hours or days, depending to a great extent on the reactivity of the phenolic compounds employed.

The resulting products can be isolated by usual methods, for example by filtration, solvent extraction or distillation preferably under reduced pressure.

Depending on the envisaged end-use, it may be advantageous to use the crude resulting product or to purify it by distillation or crystallization in an organic solvent.

The starting materials of the formulae IV, V and VI are partly known products and can be prepared according to known methods. Specific references for the preparation of halosilanes according to the formula IV are "Comprehensive Organometallic Chemistry", Editors: G. Wilkinson, F. G. A. Stone and E. W. Abel, Pergamon Press, New York, 1982, pp. 10–12 and pp. 177–185; or "Methoden der Organischen Chemie", Houben-Weyl, Editors E. Müller and O. Bayer, Jeorg Thieme Verlag, New York 1980, pp. 1–423, Band XIII/5.

The starting materials of the formula VII are partly known products and can be prepared, for example, by a transesterification reaction of one mole of a compound of the formula VIII and one mole of a compound of the formula IX

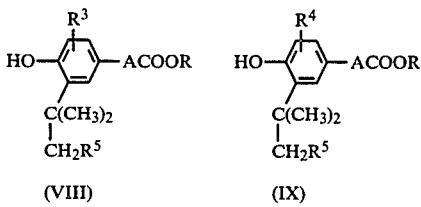

with one mole of a compound of the formula X $$HO-B-OH \qquad (X)$$

wherein A, B, $R^3$, $R^4$ and $R^5$ have the above meanings and R is a lower alkyl group.

The compounds of the formulae I and II of the present invention are particularly effective in stabilizing organic materials subject to oxidative, thermal and actinic degradation, such as plastics, polymers and resins. In addition, they exhibit improved resistance to hydrolysis due to the ortho substitution.

Substrates in which the compounds of the formulae I and II are particularly useful are polyolefins such as polyethylene and polypropylene; polystyrene, including impact polystyrene, ABS resin, SBR, isoprene, as well as natural rubber, polyesters including polyethylene terephthalate and polybutylene terephthalate, including copolymers, and lubricating oils such as those derived from mineral oil.

In general polymers which can be stabilized include:

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under (1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or -methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from, $\beta$-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadien, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamid or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymerhomologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/butadiene copolymers.

In general, the compounds of the formulae I and II of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants

1.1. Alkylated monophenols, for example, 2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-( -methylcyclohexyl)-4,6-dimethylphenol
2,6-di-octadecyl-4-methylphenol
2,4,6-tri-cyclohexylphenol
2,6-di-tert.butyl-4-methoxymethylphenol

1.2. Alkylated hydroquinones, for example, 2,6-di-tert.butyl-4-methoxyphenol
2,5-di-tert.butyl-hydroquinone
2,5-di-tert.amyl-hydroquinone
2,6-diphenyl-4-octadecyloxyphenol

1.3. Hydroxylated thiodiphenyl ethers, for example, 2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkyliden-bisphenols, for example, 2,2'-methylene-bis-(6-tert.butyl-4-methylphenol)
2,2'-methylene-bis-(6-tert.butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl)-butane
2,6-di-(3-tert.butyl-5-methyl-2-hydroxybenzyl)-4-methylphenol
1,1,3-tris-(5-tert.butyl-4-hydroxy-2-methylphenyl)-butane
1,1-bis-(5-tert.butyl-4-hydroxy-2-methylphenyl)-3-n-dodecylmercaptobutane
ethylenglycol-bis-[3,3-bis-(3'-tert.butyl-4'-hydroxyphenyl)-butyrat]
di-(3-tert.butyl-4-hydroxy-5-methylphenyl)-dicyclopentadien
di-[2-(3'-tert.butyl-2'-hydroxy-5'-methyl-benzyl)-6-tert.butyl-4-methylphenyl]-terephthalate.

1.5. Benzyl compounds, for example, 1,3,5-tri-(3,5-di-tert.butyl-4-hydroxybenzyl)-2,4,6-trimethylbenzene-di-(3,5-di-tert.butyl-4-hydroxybenzyl)sulfide
3,5-di-tert.butyl-4-hydroxybenzyl-mercapto-acetic acid isooctyl ester
bis-(4-tert.butyl-3-hydroxy-2,6-dimethylbenzyl)dithiol-terephthalate
1,3,5-tris-(3,5-di-tert.butyl-4-hydroxybenzyl)-isocyanurate
1,3,5-tris-(4-tert.butyl-3-hydroxy-2,6-dimethylbenzyl)isocyanurate
3,5-di-tert.butyl-4-hydroxybenzyl-phosphoric acid di-octadecyl ester
3,5-di-tert.butyl-4-hydroxybenzyl-phosphoric acid monoethyl ester, calcium-salt

1.6. Acylaminophenols, for example, 4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbaminate

1.7. Esters of

β-(3,5-di-tert.butyl-4-hydroxyphenyl)propionic acid with monohydric or polyhydric alcohols, for example, methanol
octadecanol
1,6-hexanediol
neopentylglycol
thiodiethyleneglycol
diethyleneglycol
triethyleneglycol
pentaerythritol
tris-hydroxyethyl isocyanurate
di-hydroxyethyl oxalic acid
diamide

1.8. Ester of

β-(5-tert.butyl-4-hydroxy-3-methylphenyl)propionic acid with monohydric or polyhydric alcohols, for example, methanol
octadecanol
1,6-hexanediol
neopentylglycol
thiodiethyleneglycol
diethyleneglycol
triethyleneglycol
pentaerytritol
tris-hydroxyethyl isocyanurate
di-hydroxyethyl oxalic acid
diamide

1.9. Amides of

β-(3,5-di-tert.butyl-4-hydroxyphenyl)propionic acid for example,

N,N'-di-(3,5-di-tert.butyl-4-hydroxyphenylpropionyl)-hexamethylendiamine
N,N'-di-(3,5-di-tert.butyl-4-hydroxyphenylpropionyl)-trimethylendiamine
N,N'-di-(3,5-di-tert.butyl-4-hydroxyphenylpropionyl)-hydrazine

2. UV absorbers and light stabilisers

2.1. 2-(2'-Hydroxyphenyl)-benztriazoles, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'- tert.butyl-, 4'-octoxy, 3',5'-di-tert.amyl-, 3',5'-bis-(α,α-dimethylbenzyl)-derivative.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivative.

2.3. Ester of optionally substituted benzoic acids for example, phenyl salicylate, 4-tert.butyl-phenylsalicilate, octylphenyl salicylate, dibenzoylresorcinol, bis-(4-tert.butylbenzoyl)-resorcinol, benzoylresorcinol, 3,5-di-tert.butyl-4-hydroxybenzoic acid 2,4-di-tert-.butyl-phenyl ester and 3,5-di-tert.-butyl-4-hydroxybenzoic acid hexadecyl ester.

2.4. Acrylates, for example, -cyano-β,β-diphenylacrylic acid ethyl ester or isooctyl ester, -carbomethoxy-cinnamic acid methyl ester, -cyano-β-methyl-p-methoxy-cinnamic acid methyl ester or butyl ester, -carbomethoxy-p-methoxy-cinnamic acid methyl ester, N-(β-carbomethoxy-β-cyanovinyl)-2-methylindoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert-.butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)-sebacate bis-(1,2,2,6,6-pentamethylpiperidyl)-sebacate n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylendiamine and 4-tert.octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7 Oxalic acid diamides, for example, 4,4'-di-octyloxyoxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis (3-dimethylaminopropyl)oxalamide, 2-ethoxy-5-tert.butyl-2'-ethyloxanilide and its mixture with 2-ethoxy-2'-ethyl-5,4'-di-tert.butyloxanilide and mixtures of ortho- and para-methoxy- as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino-1,2,4-triazole, bis-benzyliden-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythrit diphosphite, tris-(2,4-di-tert.butylphenyl) phosphite, di-isodecylpentaerythrit diphosphite, di-(2,4-di-tert.butylphenyl)pentaerythrit diphosphite, tristearyl-sorbite triphosphite, tetrakis-(2,4-di-tert.butylphenyl)-4,4'-diphenylylendiphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythrit-tetrakis(β-dodecylmercapto)-propionate.

6. Polyamide stabilisers, for example copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticizers, lubricants, emulsifiers, pigments, optical brighteners, flameproofing agents, anti-static agents, blowing agents and thiosynergists such as dilaurylthiodipropionate or distearylthiodipropionate.

The following examples illustrate the embodiment of this invention. In these examples, all parts given are by weight unless otherwise specified.

EXAMPLE 1

Methyl-di-(4-n-dodecyloxycarbonyl-2,6-di-tert-butyl phenoxy)-silane

A 300 ml flame-dried flask equipped with condenser, magnetic agitation, thermometer and slow-addition funnel is charged with a mixture of 2.30 grams (0.02 mol) of dichloromethylsilane, 4.04 grams (0.04 mol) of triethylamine and 25 ml of toluene. The mixture is treated at 0° to 5° C. over a 25 minute period with 16.7 grams (0.40 mol) of n-dodecyl 2,6-di-tert-butyl-4-hydroxybenzoate in 100 ml of toluene. The resultant mixture is then allowed to warm to ambient temperature and is stirred until the disappearance of the phenolic OH absorption in the IR spectrum. The mixture is filtered and the filtrate is concentrated in vacuo. The residue is purified by recrystallization from a 1:1 mixture of acetonitrile and toluene to give 2.70 grams of a colorless solid mp 55.5°–56.5° C., and having the following formula

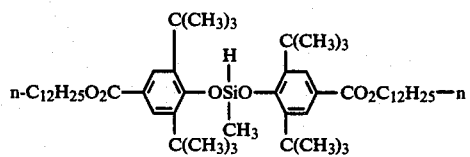

Analysis: Calculated for $C_{55}H_{94}O_6Si$: C 75.12%; H 10.77%; Found: C 74.96%; H 10.54%.

EXAMPLE 2

Preparation of a copolymer from 1,6-hexanediol bis(3,5-di-tert-butyl-4-hydroxybenzoate) and dimethyldichlorosilane A one-liter flame dried flask equipped with condenser, magnetic agitation, thermometer, nitrogen blanket and addition funnel is charged with a mixture of 29.1 grams (0.05 mol) of 1,6-hexanediol bis (3,5-di-tert-butyl-4-hydroxybenzoate) in 300 ml of tetrahydrofuran. The mixture is treated at ambient temperature with a mixture of 2.4 grams (0.10 mol) of sodium hydride in 100 ml of tetrahydrofuran. After stirring for 24 hours at ambient temperature, the mixture is heated at 40°–50° C. for two hours. The resultant mixture is treated with a mixture of 6.45 grams (0.05 mol) of dichlorodimethylsilane and 0.32 grams (0.001 mol) of tetrabutyl ammonium bromide in 25 ml of tetrahydrofuran. The mixture is then heated at 40° C. until the disappearance of the phenolic OH absorption in the IR spectrum. After cooling, the mixture is filtered and the filtrate is concentrated in vacuo. The residue is then purified by dry column chromatography on silica gel (toluene eluent) to give 17.5 grams of a colorless solid, mp 67°–69° C.

Analysis: Calculated for $C_{74}H_{12}O_{112}Si$: C 71.43%; H 9.15%; Found: C 71.01%; H 9.10%.

EXAMPLE 3

Bis (2,6-di-tert-butyl-4-n-hexyloxycarbonylphenoxy)dimethylsilane

A 500 ml flame dried flask equipped with condenser, magnetic agitation, thermometer, nitrogen blanket and addition funnel is charged with a mixture of 1.2 grams (0.05 mol) of sodium hydride in 100 ml of tetrahydrofuran. The mixture is treated at ambient temperature with a mixture of 16.7 grams (0.05 mol) of n-hexyl-3,5-di-tert-butyl-4-hydroxybenzoate in 50 ml of tetrahydrofuran. The resultant suspension is then stirred until it is homogeneous and gas evolution had ceased (approximately 2 hours). The resultant solution is admixed at ambient temperature with a mixture of 3.23 grams (0.025 mol) of dichlorodimethylsilane and 1.1 grams (0.0025 mol) of 15-crown-5 in 25 ml of tetrahydrofuran The reaction mixture is heated at 40° C. until the disappearance of the phenolic OH absorption in the IR spectrum. Upon cooling, the mixture is filtered and the filtrate is concentrated in vacuo. The residue is purified by flash chromatography on silica gel (1:1 heptane-toluene eluent) to give 7.37 grams of a colorless syrup having the formula

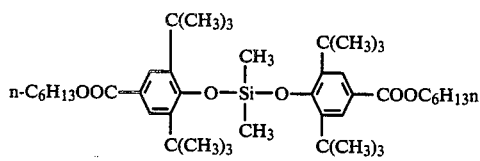

Analysis: Calculated for $C_{44}H_{72}O_6Si$: C 72.9%; H 10.0%; Found: C 73.1%; H 9.9%.

EXAMPLE 4

Bis (2,6-di-tert-butyl-4-n-dodecyloxycarbonylphenoxy)-dimethylsilane

The procedure of Example 3 is repeated using 1.32 grams (0.055 mol) of sodium hydride, 20.93 grams (0.05 mol) of n-dodecyl 3,5-di-tert-butyl-4-hydroxybenzoate, 1.1 grams (0.0025 mol) of 15-crown-5, 3.23 grams (0.025 mol) of dichlorodimethylsilane and 150 ml of tetrahydrofuran. The residue is purified by flash chromatography on silica gel (35 parts of heptane: 5 parts of ethyl acetate eluent) to give 8.4 grams of a colorless syrup having the formula

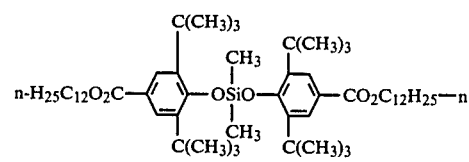

Analysis: Calculated for $C_{56}H_{96}O_6Si$: C 75.3%; H 10.8%; Found: C 75.5%; H 10.9%.

EXAMPLE 5

Bis (2,6-di-tert-butyl-4-methoxycarbonylphenoxy)dimethylsilane

The procedure of Example 3 is again repeated using 5.28 grams (0.22 mol) of sodium hydride, 58.87 grams (0.2 mol) of methyl 3-5-di-tert-butyl-4-hydroxybenzoate, 2.2 grams (0.1 mol) of 15-crown-5, 12.9 grams (0.1 mol) of dichlorodimethylsilane and 200 ml of tetrahydrofuran. The residue is purified by recrystallization from a 1:1 mixture of toluene: acetonitrile to give 34.4 grams of a colorless solid, mp 197°–198° C., and having the formula

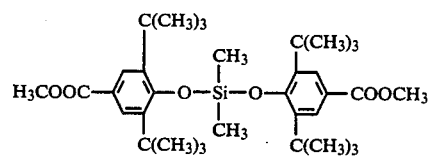

Analysis: Calculated for $C_{34}H_{52}O_6Si$: C 69.8%; H 9.0%; Found: C 70.2%; H 9.1%.

EXAMPLE 6

Bis (2,6-di-tert-butyl-4-n-octadecyloxycarbonylphenoxy)-dimethylsilane

The procedure of Example 3 is repeated using 2.64 grams (0.11 mol) of sodium hydride, 50.3 grams (0.1 mol) of n-octadecyl 3,5-di-tert-butyl-4-hydroxybenzoate, 1.1 grams of (0.005 mol) 15-crown-5, 6.4 grams (0.5 mol) of dichlorodimethylsilane and 200 ml of tetrahydrofuran. The residue is purified by flash chromatography on silica gel (90 parts of heptane: 10 parts of toluene eluent) to give 6.70 grams of a colorless solid, mp 68.5°–69.5° C., and having the formula

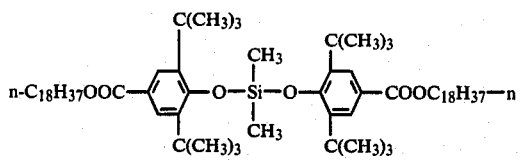

Analysis: Calculated for $C_{68}H_{120}O_6Si$: C 76.9%; H 11.4%; Found: C 77.0%; H 11.4%.

EXAMPLE 7

Dimethyl-bis{2,6-di-tert-butyl-4-[2-(methoxycarbonyl)ethyl]-phenoxy}-silane

To a stirred suspension of 3.06 grams of sodium hydride in 25 ml of tetraethylene glycol dimethylether is added dropwise a solution of methyl 3-(3,5-di-tert.-butyl-4-hydroxyphenyl)-propanoate in 115 ml of tetraethylene glycol dimethylether. The reaction mixture is stirred until hydrogen evolution is complete and then to the resultant reaction mixture is added sequentially 1.65 g of 15-crown-5 and 4.84 g of dichlorodimethylsilane. The reaction mixture is heated at 70° C. for 26 hours and then the cooled reaction mixture is partitioned between 1 liter of diethyl ether and 1 liter of water. The organic phase is separated and then extracted three times with water. The organic phase is dried over anhydrous sodium sulfate and the residue is recrystallized from acetonitrile to give 22.4 g (46%) of a white solid, mp 122°–129° C., of the following formula

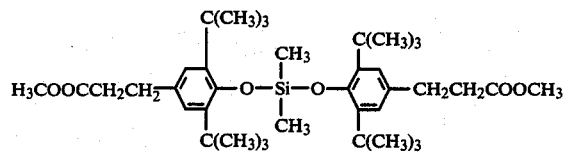

Analysis: Calculated for $C_{38}H_{60}O_6Si$: C 71.2%; H 9.44%; Found: C 72.5%; H 9.3%.

EXAMPLE 8

Dimethyl-bis{2,6-di-tert-butyl-4-[2-(octadecyloxycarbonyl)ethyl].phenoxy}-silane The procedure of Example 7 is followed using 3.06 grams of sodium hydride, 39.82 grams of n-octadecyl 3-(3,5-tert-butyl-4-hydroxyphenyl)-propanoate, 1.65 grams of 15-crown-5, and 4.84 grams of dichlorodimethylsilane. Unreacted n-octadecyl 3-(3,5-di-tert.-butyl-4-hydroxyphenyl)-propanoate is removed by bulb to bulb distillation and the residue is recrystallized from 2-propanol to give 14.4 grams (34%) of a white solid, mp. 50°–55° C., of the following formula

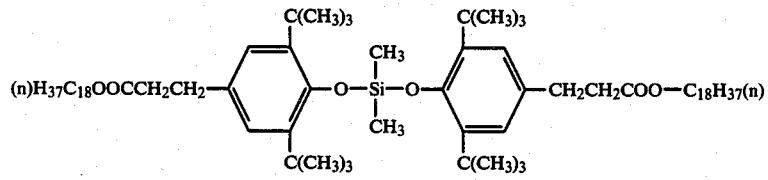

Analysis: Calculated for $C_{72}H_{128}O_6Si$: C, 77.4%; H, 11.4%; Found: C, 77.1%; H, 11.5%.

EXAMPLE 9

Unstabilized polypropylene powder (Hercules Profax ® 6501) is thoroughly blended with the indicated amount of additive. The blended materials are then milled on a two roll mill at 182° C. for five minutes, after which time the stabilized polypropylene is sheeted from the mill and allowed to cool. The milled polypropylene is then cut into pieces and compression molded on a hydraulic press at 220° C. and 175 psi ($1.2 \times 10^6$ Pa) into 5 mil (0.127 mm) films. The samples are exposed in a fluorescent sunlight/black light chamber until failure. Failure is taken as hours required to reach 0.5 carbonyl absorbance by infrared spectroscopy on the exposed films.

| Additive Compound of | Additive Conc. (% by weight) | FS/BL Test Results (Hours to Failure) |
|---|---|---|
| None | — | 250 |
| Example 1 | 0.3 | 560 |
| Example 2 | 0.3 | 490 |
| Example 3 | 0.3 | 470 |
| Example 4 | 0.3 | 600 |
| Example 5 | 0.3 | 500 |
| Example 6 | 0.3 | 500 |

These data clearly indicate the effective stabilization of the compounds of this invention.

EXAMPLE 10

The oxidation stability of the milled polypropylene sample from Example 9 containing 0.3% by weight of the compound of Example 2 on plaques of 25 mil (0.635 mm) thickness measured on exposure of the sample to air in a forced draft oven at 150° C. The plaques are considered to have failed on showing the first signs of decomposition (e.g., cracking or brown edges).

| Additive/ Compound of | Additive Concentration (%) | Oxidative Stability Time to Failure (Hrs) |
|---|---|---|
| Base resin | — | <20 |
| Example 2 | 0.3 | 20 |

These data clearly indicate the effective stabilization of the compounds of this invention.

EXAMPLE 11

Stabilization of PVC

The PVC resin Geon 85862 natural powder containing a butyl tin mercaptide thermal stabilizer is blended with 5 phr of $TiO_2$ and this formulation is used as a control (A). One phr each of the stabilizers of this instant invention is added to a portion of A. These stabilized formulations are extruded and compression molded test plaques are made and tested by accelerated aging in a Xenon weatherometer. The yellowness index color of the plaques is determined as shown in the next table.

Light Stabilization of Rigid PVC

Base Resin—B. F. Goodrich Geon 85862 containing butyl tin mercaptide thermal stabilizer.
Test Samples—Compression molded plaques.

Xenon Weatherometer Exposure

|  | Yellowness Index | | |
| --- | --- | --- | --- |
|  | Initial | 770 Hrs | 2030 Hrs |
| Base Resin + 5 phr TiO₂ (Rutile) (A) | 7.3 | 13.5 | 29.4 |
| Base Resin + 5 phr TiO₂ + 1 phr Example 2 | 7.3 | 9.5 | 20.2 |
| Base Resin + 5 phr TiO₂ (Rutile) + 1 phr of Example 4 | 7.5 | 10.6 | 22.2 |
| Base Resin + 5 phr TiO₂ 1 phr of Example 6 | 7.3 | 9.5 | 20.2 |

The results shown that oxidation of the base resin containing 5 phr TiO₂ (formulation A) is significantly reduced by the addition of 1 phr of the compounds of this instant invention as shown by the reduced color of the plaques.

Summarizing, it is seen that this invention provides novel silica-containing compounds which exhibit effective stabilization activity. Variations may be made in proportions, procedures and materials without departing from the scope of the invention as defined by the following claims.

What is claimed is:
1. A compound of the formulae I and II

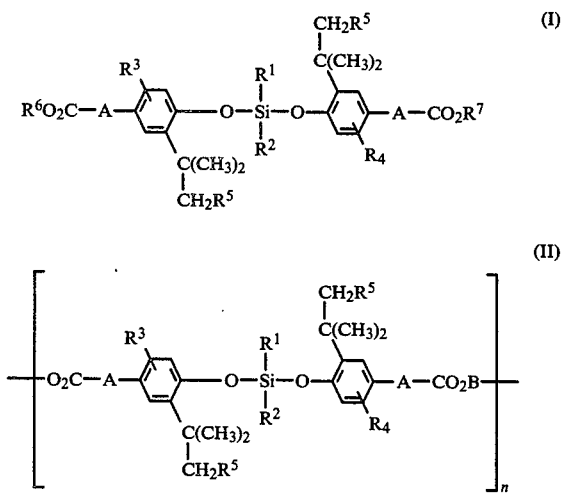

wherein
$R^1$, $R^2$, $R^3$, $R^4$ and $R^5$ are independently hydrogen, alkyl of 1 to 18 carbon atoms cycloalkyl of 5 to 8 carbon atoms, phenyl, phenyl substituted by alkyl of 1 to 18 carbon atoms, aralkyl of 7 to 9 carbon atoms or said aralkyl substituted by alkyl of 1 to 12 carbon atoms, $R^6$ and $R^7$ are independently alkyl having 1 to 30 carbon atoms, cycloalkyl of 5 to 8 carbon atoms, phenyl, phenyl substituted by alkyl of 1 to 18 carbon atoms, aralkyl of 7 to 9 carbon atoms or said aralkyl substituted by alkyl of 1 to 12 carbon atoms;
A is a direct bond, a methylene or an ethylene radical,
B is an alkanediyl radical of 2 to 10 carbon atoms, the radical of formula —CH₂CH₂—S—CH₂CH₂— or of the formula III $$-CH_2CH_2-(O-CH_2CH_2)_m- \qquad (III),$$

wherein m is an integer from 1 to 4, B also denotes a phenylene radical or a biphenylene radical interrupted by an oxygen or a sulfur atom or by the group of formula —C(CH₃)₂—; and
n is an integer from 2 to 100.

2. The compound of the formulae I and II, in which $R^1$ and $R^2$ are hydrogen or alkyl of 1 to 4 carbon atoms, $R^3$ and $R^4$ are hydrogen or alkyl of 1 to 6 carbon atoms, $R^5$ is hydrogen, $R^6$ and $R^7$ are alkyl of 1 to 18 carbon atoms, A is a direct bond or an ethylene radical, B is a hexamethylene radical and n is a number from 2 to 10.

3. The compound of the formulae I and II, in which $R^1$ and $R^2$ are hydrogen or methyl, $R^3$ and $R^4$ are tert.-butyl and are in ortho position to the phenolic oxygen atom, $R^5$ is hydrogen, and $R^6$ and $R^7$ are alkyl of 10 to 18 carbon atoms, A is a direct bond, B is a hexamethylene radical and n is a number from 2 to 5.

4. The compound of claim 1 which corresponds to formulae I.

5. Methyl-di-(4-n-dodecyloxycarbonyl-2,6-di-tert-butyl phenoxy)-silane according to claim 4.

6. Bis (2,6-di-tert-butyl-4-n-hexyloxycarbonyl-phenoxy)-dimethylsilane according to claim 4.

7. Bis (2,6-di-tert-butyl-4-n-dodecyloxycarbonyl-phenoxy)-dimethylsilane according to claim 4.

8. Bis (2,6-di-tert-butyl-4-methoxycarbonylphenoxy)-dimethylsilane according to claim 4.

9. Bis (2,6-di-tert-butyl-4-n-octadecyloxycarbonyl-phenoxy)-dimethylsilane according to claim 4.

10. Dimethyl-bis{2,6,-di-tert-butyl-4-[2-(methoxycarbonyl) ethyl]-phenoxy}silane according to claim 4.

11. Dimethyl-bis{2,6,-di-tert-butyl-4-[2-(octadecyloxycarbonyl) ethyl]-phenoxy}silane according to claim 4.

12. A composition of matter comprising an organic material subject to oxidative, thermal and actinic degradation selected from the group consisting of polyolefins, styrene polymers, isoprene, natural rubber, polyesters and lubricating oils stabilized with an effective stabilizing amount of a compound of the formula I and II according to claim 1.

13. A method for stabilizing an organic material against oxidative, thermal and actinic degradation selected from the group consisting of polyolefins, styrene polymers, isoprene, natural rubber, polyesters and lubricating oils which comprises incorporating into said organic material an effective stabilizing amount of a compound of formulae I and II according to claim 1.

* * * * *